(12) United States Patent
Baker et al.

(10) Patent No.: US 10,945,679 B2
(45) Date of Patent: Mar. 16, 2021

(54) MODULAR MONITORING SMART BED

(71) Applicant: Welch Allyn, Inc., Skaneateles Falls, NY (US)

(72) Inventors: Steven D. Baker, Beaverton, OR (US); Rachel Williamson, Batesville, IN (US); Samuel Lai, Singapore (SG); Kristen L. Stebbins, Cicero, NY (US); Philippe Kaikenger, Pluvigner (FR); Catherine King, Fayetteville, NY (US); Leigh Scott Coleman, II, Portland, OR (US); Alisa Robinson Salibra, Fayetteville, NY (US); Todd Ventrola, Liberty Township, OH (US); Dan R. Tallent, Hope, IN (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 165 days.

(21) Appl. No.: 15/883,428

(22) Filed: Jan. 30, 2018

(65) Prior Publication Data

US 2018/0214091 A1 Aug. 2, 2018

Related U.S. Application Data

(60) Provisional application No. 62/608,312, filed on Dec. 20, 2017, provisional application No. 62/452,698, filed on Jan. 31, 2017.

(51) Int. Cl.
*A61B 5/00* (2006.01)
*A61G 7/018* (2006.01)
(Continued)

(52) U.S. Cl.
CPC ............ *A61B 5/746* (2013.01); *A61B 5/6891* (2013.01); *A61G 7/002* (2013.01); *A61G 7/015* (2013.01);
(Continued)

(58) Field of Classification Search
None
See application file for complete search history.

(56) References Cited

U.S. PATENT DOCUMENTS 5,269,030 A * 12/1993 Pahno ................. A61G 7/0005
4/480
5,664,270 A 9/1997 Bell et al.
(Continued)

FOREIGN PATENT DOCUMENTS

TW 201407164 A 2/2014
WO 2009129306 A1 10/2009
(Continued)

OTHER PUBLICATIONS

Doty, TJ et al., The Wearable Multimodal Monitoring System: a Platform to Study Falls and Near-falls in the Real-word, in Human Aspects of IT for the Aged Population, Design for Everyday Life: pp. 412-422, Springer International Publishing, 2013, 12pgs.
(Continued)

*Primary Examiner* — Carl H Layno
*Assistant Examiner* — Manolis Pahakis
(74) *Attorney, Agent, or Firm* — Merchant & Gould P.C.

(57) ABSTRACT

A patient monitoring system includes sensors, a patient support assembly, and a gateway device and/or control module. Example sensors include physiological sensors and patient status devices. The sensors acquire patient-related data. Patient related action is determined based on the patient-related data.

11 Claims, 7 Drawing Sheets

(51) Int. Cl.
*G16H 10/60* (2018.01)
*A61G 7/015* (2006.01)
*A61G 7/002* (2006.01)
*G16H 50/30* (2018.01)
*G16H 40/63* (2018.01)
*G16H 50/20* (2018.01)
*A61B 5/11* (2006.01)
*A61B 5/024* (2006.01)
*A61B 5/08* (2006.01)
*A61B 5/01* (2006.01)
*A61B 5/021* (2006.01)
*A61B 5/145* (2006.01)
*A61B 5/0205* (2006.01)
*A61G 7/057* (2006.01)

(52) U.S. Cl.
CPC ............ *A61G 7/018* (2013.01); *G16H 10/60* (2018.01); *G16H 40/63* (2018.01); *G16H 50/20* (2018.01); *G16H 50/30* (2018.01); *A61B 5/01* (2013.01); *A61B 5/021* (2013.01); *A61B 5/024* (2013.01); *A61B 5/02055* (2013.01); *A61B 5/0816* (2013.01); *A61B 5/1115* (2013.01); *A61B 5/14542* (2013.01); *A61B 5/4815* (2013.01); *A61B 5/4848* (2013.01); *A61B 2560/0214* (2013.01); *A61G 7/05769* (2013.01); *A61G 7/05784* (2016.11); *A61G 2200/30* (2013.01); *A61G 2205/00* (2013.01); *A61G 2205/60* (2013.01)

(56) References Cited

U.S. PATENT DOCUMENTS

| | | | |
|---|---|---|---|
| 6,840,955 B2 | 1/2005 | Ein | |
| 7,562,458 B1* | 7/2009 | Clark, Jr. | A61G 7/018 33/333 |
| 7,833,188 B2* | 11/2010 | Gerber | A61J 15/0003 5/610 |
| 7,884,735 B2 | 2/2011 | Newkirk | |
| 7,942,825 B2 | 5/2011 | Ranganathan et al. | |
| 8,087,254 B2 | 1/2012 | Arnold | |
| 8,281,433 B2 | 10/2012 | Riley et al. | |
| 8,397,393 B2* | 3/2013 | Johnson | A61G 7/018 33/333 |
| 8,475,368 B2 | 7/2013 | Bao | |
| 8,752,220 B2 | 6/2014 | Soderberg et al. | |
| 8,957,777 B2 | 2/2015 | Baker et al. | |
| 9,028,407 B1* | 5/2015 | Bennett-Guerrero | A61B 5/1121 600/301 |
| 9,132,031 B2 | 9/2015 | Levinson et al. | |
| 9,233,038 B2 | 1/2016 | Gibson et al. | |
| 9,852,265 B1* | 12/2017 | Treacy | G16H 10/60 |
| 10,600,204 B1* | 3/2020 | Rush | G06T 7/74 |
| 2003/0046762 A1 | 3/2003 | Stolpmann | |
| 2004/0010390 A1* | 1/2004 | Kelly, Jr. | G08B 21/0288 702/150 |
| 2005/0149153 A1 | 7/2005 | Nakase | |
| 2005/0267339 A1 | 12/2005 | Beckmann et al. | |
| 2006/0021240 A1* | 2/2006 | Horgan | A61B 5/1071 33/366.11 |
| 2006/0028350 A1* | 2/2006 | Bhai | G01G 19/445 340/666 |
| 2006/0049936 A1* | 3/2006 | Collins, Jr. | G08C 19/00 340/539.11 |
| 2006/0101581 A1* | 5/2006 | Blanchard | A61G 7/001 5/713 |
| 2006/0202816 A1 | 9/2006 | Crump et al. | |
| 2007/0143920 A1* | 6/2007 | Frondorf | A61G 7/0513 5/81.1 R |
| 2008/0077201 A1 | 3/2008 | Levinson et al. | |
| 2008/0109255 A1* | 5/2008 | Allen | G16H 40/20 705/2 |
| 2008/0235872 A1* | 10/2008 | Newkirk | G06F 3/0481 5/600 |
| 2009/0069642 A1 | 3/2009 | Gao et al. | |
| 2009/0149927 A1 | 6/2009 | Kneuer et al. | |
| 2010/0073168 A1* | 3/2010 | Tallent | A61G 7/018 340/573.1 |
| 2010/0298658 A1 | 11/2010 | McCombie | |
| 2010/0298718 A1* | 11/2010 | Gilham | H04W 16/10 600/484 |
| 2011/0024076 A1 | 2/2011 | Lachenbruch et al. | |
| 2011/0068939 A1 | 3/2011 | Lachenbruch | |
| 2011/0208076 A1* | 8/2011 | Fong | A61B 5/0205 600/509 |
| 2011/0234411 A1* | 9/2011 | Harrington | A61G 7/05 340/573.4 |
| 2011/0263950 A1 | 10/2011 | Larson et al. | |
| 2011/0301440 A1* | 12/2011 | Riley | A61B 5/02055 600/301 |
| 2012/0025992 A1* | 2/2012 | Tallent | G08B 21/22 340/573.4 |
| 2012/0075464 A1* | 3/2012 | Derenne | A61B 5/7445 348/135 |
| 2012/0089419 A1* | 4/2012 | Huster | A61G 7/001 705/3 |
| 2012/0154152 A1* | 6/2012 | Rantala | A61B 5/04018 340/573.1 |
| 2012/0232416 A1* | 9/2012 | Gilham | G16H 40/63 600/515 |
| 2012/0253142 A1* | 10/2012 | Meger | A61B 5/7415 600/301 |
| 2013/0036549 A1 | 2/2013 | McKlarney | |
| 2013/0090571 A1 | 4/2013 | Nourani et al. | |
| 2013/0263378 A1* | 10/2013 | O'Keefe | A61G 7/002 5/713 |
| 2014/0039351 A1* | 2/2014 | Mix | A61B 5/6892 600/587 |
| 2014/0041119 A1* | 2/2014 | Thodupunuri | A61G 7/08 5/510 |
| 2014/0059766 A1* | 3/2014 | Gibson | A61G 7/05 5/600 |
| 2014/0059770 A1* | 3/2014 | Williamson | G16H 40/63 5/617 |
| 2014/0066815 A1* | 3/2014 | Williamson | A61B 5/6892 600/595 |
| 2014/0237722 A1 | 8/2014 | Gibson et al. | |
| 2014/0260331 A1 | 9/2014 | Lofy et al. | |
| 2014/0323816 A1 | 10/2014 | Soderberg | |
| 2014/0345060 A1 | 11/2014 | Ribble et al. | |
| 2015/0051673 A1 | 2/2015 | Rivas Tapia | |
| 2015/0081335 A1* | 3/2015 | Dixon | G06Q 50/22 705/3 |
| 2015/0137968 A1* | 5/2015 | Rusin | G08B 25/001 340/506 |
| 2015/0157521 A1* | 6/2015 | Williams | A47C 27/088 5/81.1 R |
| 2015/0164438 A1* | 6/2015 | Halperin | G06Q 10/06398 340/573.1 |
| 2015/0281659 A1* | 10/2015 | Hood | A61G 7/0524 348/143 |
| 2016/0022218 A1* | 1/2016 | Hayes | A61B 5/4809 600/301 |
| 2016/0103967 A1* | 4/2016 | Bulut | G16H 70/40 705/2 |
| 2016/0120716 A1 | 5/2016 | Ribble et al. | |
| 2016/0220197 A1* | 8/2016 | Rantala | A61B 5/746 |
| 2016/0350489 A1* | 12/2016 | Ribble | G16H 40/20 |
| 2017/0245656 A1 | 8/2017 | Ribble et al. | |
| 2017/0245797 A1 | 8/2017 | Quinn | |
| 2018/0000633 A1 | 1/2018 | Coleman, II et al. | |
| 2018/0214091 A1* | 8/2018 | Baker | A61B 5/6891 |

(56) References Cited

U.S. PATENT DOCUMENTS

| | | | |
|---|---|---|---|
| 2019/0053707 A1* | 2/2019 | Lane | A61G 7/05 |
| 2020/0211360 A1* | 7/2020 | Baker | A61B 5/024 |

FOREIGN PATENT DOCUMENTS

| | | | |
|---|---|---|---|
| WO | 2012051628 A1 | 4/2012 | |
| WO | 2014047310 A1 | 3/2014 | |
| WO | 2015074007 A1 | 5/2015 | |
| WO | 2015148225 A2 | 10/2015 | |
| WO | 2015164456 A2 | 10/2015 | |

OTHER PUBLICATIONS

Jiang, C., A Smart and Minimum-intrusive Monitoring Framework Design for Health Assessment of the Elderly, Doctoral dissertation, University of Cincinnati, Apr. 2015, 124pgs.

Versacare(R) Med Surg Bed, http://www.hill-rom.com/usa/Products/Category/Hospital-Beds/VersaCare-med-surg-peds/Date Accessed: Dec. 28, 2015, 3pgs.

Penn Medicine Tests Wearable Patient Monitor in Hospital, http://www.summitdata.com/blog/penn-medicine-tests-wearable-patient-monitor-hospital/, Jul. 31, 2015, 2pgs.

Appelboom, G., et al., The Promise of Wearable Activity Sensors to Define Patient Recovery, Journal of Clinical Neuroscience, 21(7): 1089-1093, Publication Date: Jul. 2014, 6pgs.

U.S. Appl. No. 62/576,275, filed Oct. 24, 2017, 36pgs.

Lanata, Antonio et al., Complexity Index From a Personalized Wearable Monitoring System for Assessing Remission in Mental Health, IEEE Journal of Biomedical and Health Informatics—Sep. 2014, 8 pages.

Search Report for European Patent Application No. 16 20 7369, dated Apr. 24, 2017, 7pgs.

\* cited by examiner

MODULAR MONITORING SMART BED

CROSS-REFERENCE TO RELATED APPLICATIONS

The present application claims priority to U.S. Provisional Patent Application No. 62/452,698, filed on Jan. 31, 2017, and U.S. Provisional Patent Application No. 62/608,312, filed on Dec. 20, 2017, the disclosures of which are hereby incorporated by reference in their entireties.

INTRODUCTION

Some errors and injuries in medical facilities, such as hospitals, are the result of patient falls, medical errors, infections, and respiratory failure. These patient safety issues can result in serious injury, death, and non-reimbursable costs in the billions of dollars per year. Thus, medical facilities seek to build a culture of patient safety with improved patient outcomes.

SUMMARY

Embodiments of the disclosure are directed to a patient monitoring system. In one aspect, a patient monitoring system includes a wearable sensor configured to acquire physiological data of a patient, a patient support assembly in communication with the wearable sensor, and a gateway device in communication with the patient support assembly. The gateway device includes a processing unit and system memory. The system memory includes instructions that, when executed by the processing unit, cause the gateway device to receive physiological data and patient movement data from one or more of the wearable sensor and the patient support assembly; using the physiological data and the patient movement data received from the patient support assembly, determine patient status; based on the patient status, determine patient-related action; after a period of time, receive updated physiological data and updated patient movement data from one or more of the patient support assembly; using the updated physiological data and updated patient movement data, determine updated patient status; and, based on the updated patient status, determine additional patient-related action.

In another aspect, a patient monitoring and support system is disclosed. The example patient monitoring and support system includes a patient support assembly, a patient status device, and a control module. The patient support assembly is arranged to support a patient and the patient status device is configured to obtain patient status data. The control module includes a processing unit and memory. The memory stores instructions that, when executed by the processing unit, cause the control module to: receive the patient status data from the patient status device; analyze the patient status data to determine an updated condition of the patient; and, based on the updated condition of the patient, adjust an alarm setting.

In another aspect, a computer-implemented method for patient monitoring is disclosed. The example method includes: receiving physiological data of a patient from a patient support assembly; determining patient status using the physiological data; based on the patient status, determining patient-related action; receiving updated physiological data of the patient; receiving patient orientation data; determining updated patient status using the updated physiological data of the patient and the patient orientation data; and based on the updated patient status, determining an additional patient-related action.

The details of one or more embodiments are set forth in the accompanying drawings and the description below. Other features, objects, and advantages of these embodiments will be apparent from the description, drawings, and claims.

DESCRIPTION OF THE FIGURES

The following drawing figures, which form a part of this application, are illustrative of described technology and are not meant to limit the scope of the disclosure in any manner.

DETAILED DESCRIPTION

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

Broadly, the present disclosure is directed to improving patient outcomes with an integrated patient care system. Typical patient care environments, such as hospitals and clinical settings, include sensors, patient beds, monitors, and medical records. However, the aforementioned components are not always integrated or capable of communicating. As a result, data acquired or stored by one component cannot necessarily be accessed and utilized by other components. Such data loss is a missed opportunity for improving patient outcomes and/or caregiver efficiency. In the systems and methods described below, these data are leveraged to proactively address and predict possible negative patient outcomes, as well as notify responsible caregivers.

In some instances, patients are moved on patient beds between wards or floors of patient care environments. Usually, different types of wards have different monitoring needs. For instance, a patient in an intensive care unit typically requires more monitoring than a patient in long term care. Some of the systems and methods described below include patient monitoring components that move as patient beds are moved about a facility, thereby enabling increases and decreases in monitoring levels provided to the patient.

Figure 1:
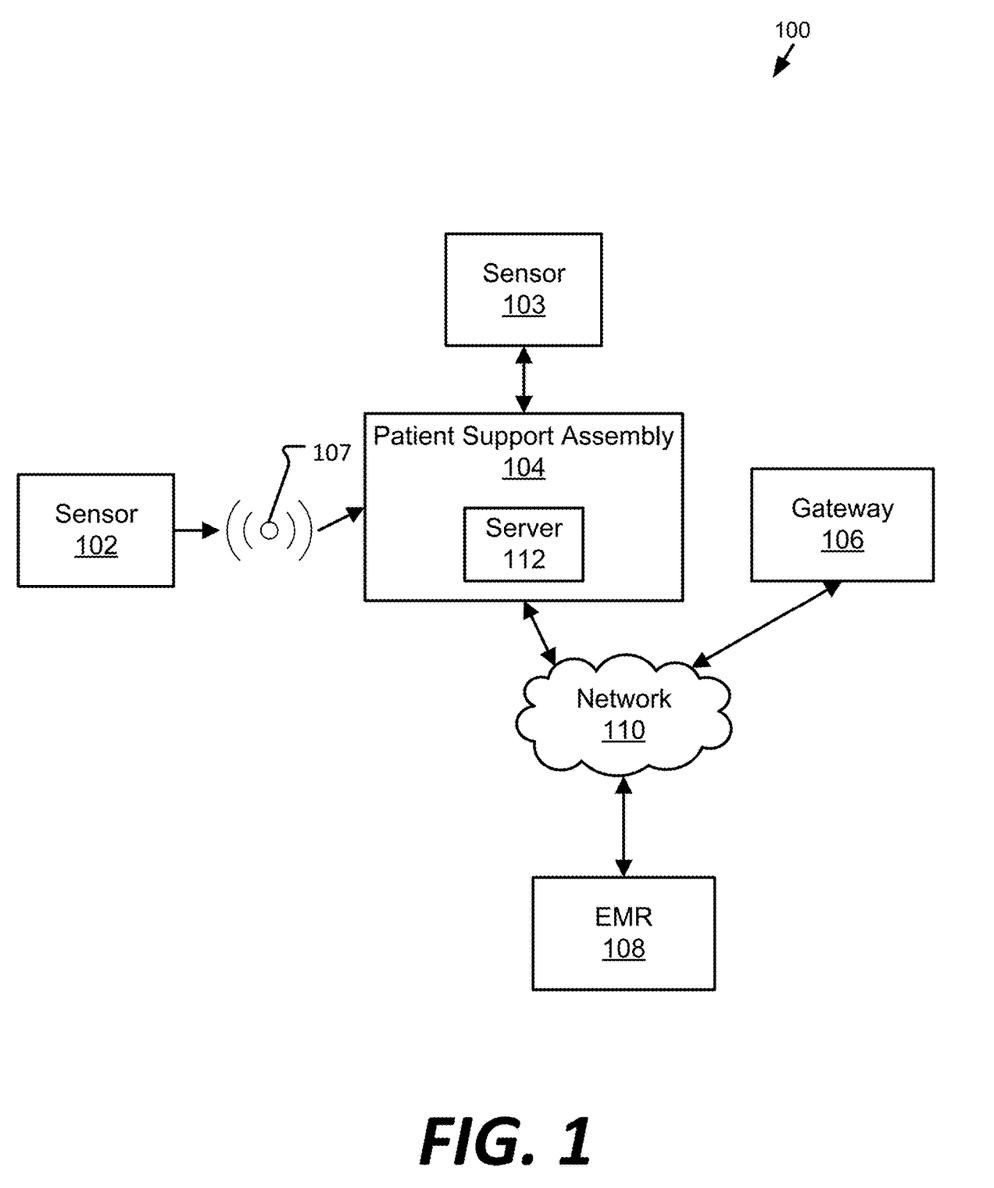
FIG. 1 is a schematic view of an example patient monitoring system.
Figure 2:
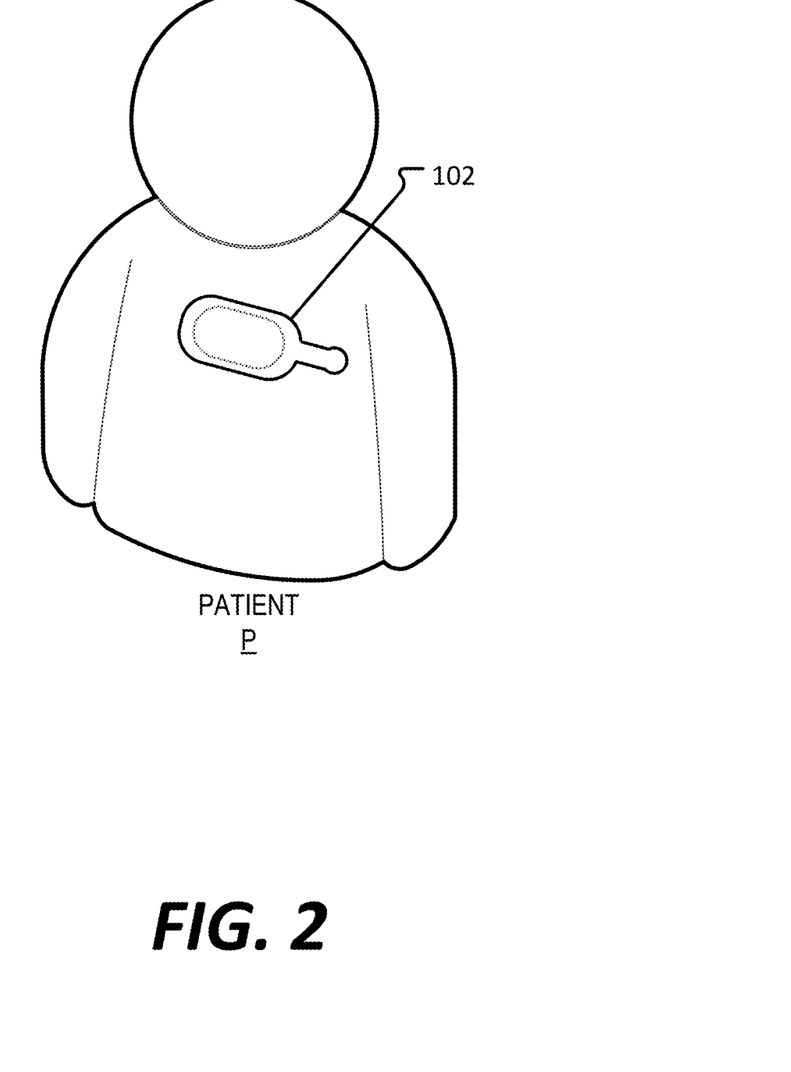
FIG. 2 illustrates an example wearable sensor used in the system of FIG. 1.
Figure 3:
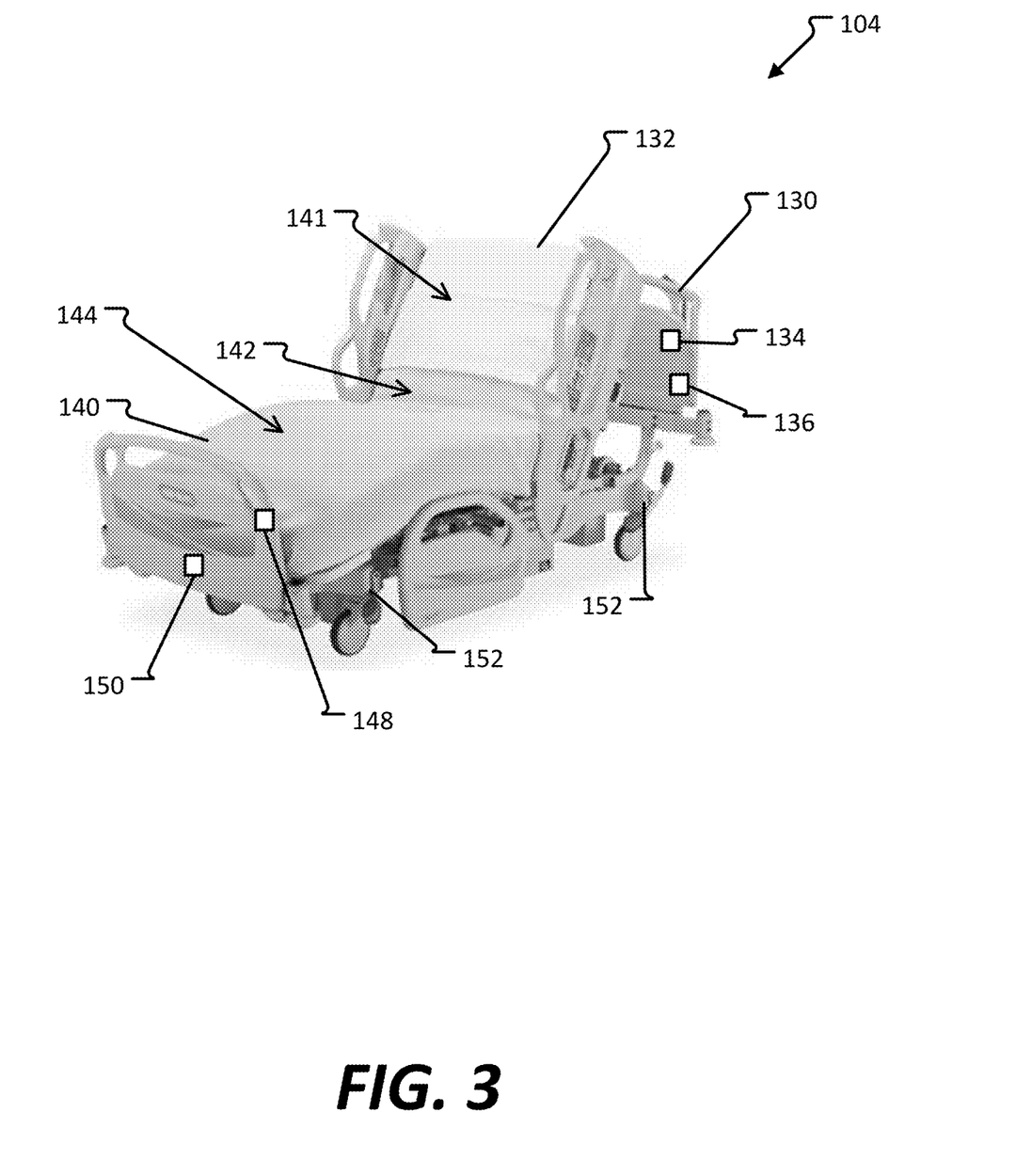
FIG. 3 illustrates an example patient support assembly used in the system of FIG. 1.

FIGS. 1-3 illustrate aspects of an example embodiment of a patient care system 100. The example patient care system 100 includes sensor 102, sensor 103, patient support assembly 104, gateway 106, and electronic medical record system (alternatively termed electronic health record, EMR/EHR) 108, and server 112. Patient support assembly 104, gateway 106, EMR 108, and server 112 are in communication with network 110. Other embodiments can include more or fewer components.

Generally, sensor 102 acquires physiological data of a patient P and communicates with patient support assembly 104. Typically, sensor 102 is wireless. Sensor 102 is capable of being removably coupled to the patient P, such as through an adhesive. Sensor 102 can also include a processing unit and memory. Sensor 102 can include a source of power such as a battery, harvest energy, or have a hybrid of the two. Alternatively, sensor 102 is without its own source of power (i.e., passive). In some instances, sensor 102 is part of a body area network (BAN) and/or associated with the patient P and/or a patient identifier. Example configurations of sensors in a body area network are described in more detail in U.S. Pat. No. 8,957,777, "Body Area Network Pairing Improvements for Clinical Workflows," the entirety of which is hereby incorporated by reference.

Sensor 102 includes one or more components capable of acquiring physiological data. Sensor 102 can sense one or more physiological signals. Example sensors include temperature, heart rate, respiration rate, blood chemistry, blood pressure, galvanic skin response, perspiration, and $SpO_2$ sensors. Other types of sensors are contemplated. Further, although a single sensor 102 is shown, multiple sensors can be used and positioned at different locations of the patient's body. Blood chemistry sensors may detect blood sugar levels, iron levels, electrolyte levels, etc. Patient position and motion data are considered physiological data in this disclosure.

In some implementations, sensor 102 is a "thin sensor," which minimizes power used by optimizing power trade-offs between communication and data processing. Thin sensors can also minimize the size and cost of sensor 102. Thin sensors transmit raw data when processing power is more expensive than transmission raw data. In other implementations, sensor 102 is a "thick sensor," which transmits processed patient vital signs parameters and waveforms when processing power is less expensive than transmission of raw data and/or when other environmental effects (such as no communication uplink) exist.

Sensor 102 can include an accelerometer in addition to the one or more physiological sensors. The accelerometer acquires data that can be used to detect patient movement and/or determine patient orientation. Patient movement can be used to assess pain levels, breathing, risk of pressure ulcers, need for patient to be rotated, provide input for the activity metric of a Braden Scale, and the like.

Sensor 102 communicates wirelessly with patient support assembly 104. Preferably, communication is via a low power channel 107, such as Bluetooth Low Energy (BLE) and/or Near Field Communication (NFC).

Sensor 102 can be configured to acquire data often, but non-continuously, for various physiological parameters. For instance, SPO2 is typically acquired continuously. But for many patients, it is acceptable to acquire periodically heart rate and oxygen saturation levels, such as every 10 or 15 minutes. Using this approach, sensor 102 can store harvested power between measurements. The time between measurements may be a dynamic function of patient state. That is, at risk patients or patients trending poorly might have measurements made more often than patients who are stable.

Sensor 102 can also be configured to obtain power from patient support assembly 104. For instance, patient support assembly 104 can be outfitted with an NFC transmitting antenna that supports powering and communication to sensor 102 devices. Still, some devices, such as a blood pressure module in turbo mode (where as many blood pressure measurements as possible are made in a limited time) may require more power than can be harvested from NFC. In those instances, another power source, such as a battery, can be used to support inflating the cuff while NFC is used to read data. Power harvested from NFC, or another wireless source, can be harvested to charge the battery when sensor 102 is not recording non-invasive blood pressure measurements, which can improve overall run time for the sensor. Blood pressure may be acquired using a cuffless blood pressure algorithm, which typically uses the time between a detected ECG signal and the pulse detection of SPO2 as the primary input to determine blood pressure. Other cuffless blood pressure algorithms use the time between two detected pulses, with the detection made by fiber optics, pressure transducers, radar, visual, optical back scatter, and optical transmission/absorbance. Wireless power transmission methods, such as Alliance for Wireless Power (A4WP) or Qi, can provide power to operate a blood pressure sensor in turbo mode. Proprietary wireless power transmission methods can be used.

Sensor 103 is a physiological sensor typically mounted or connected to patient support assembly 104. Some implementations of patient care system 100 include both patient worn, wireless sensors, such as sensor 102, and patient support assembly 104 mounted sensors, such as sensor 103. Other implementations can include only patient worn sensors. Configurations including wireless sensors provide design flexibility and continuous monitoring, for example, when a patient ambulates. Sensor 103 can be various types of physiological sensors, such as an electrocardiogram (ECG), saturated oxygen (SPO2), end-tidal carbon dioxide ($EtCO_2$), temperature, glucometer, blood pressure, etc.

Patient support assembly 104 provides support for patient P and typically includes a mattress 132, frame 130, and other components. One example of patient support assembly 104 is the Advanta™ 2 Med Surg Bed manufactured by Hill-Rom of Batesville, Ind. Patient support assembly 104 also receives data from sensor 102 and communicates the received data, along with additional patient-related data, to gateway 106.

Patient support assembly 104 can include a removable power/data module that a patient may carry while ambulating. This removable module can provide power and/or data storage for ambulatory sensors and can upload the data upon return to the patient support assembly 104. In an alternative, sensors can include sufficient power and memory to obtain and store patient data without the removable power/data module. In some implementations, power/data modules are positioned throughout the hospital that provide this functionality.

Patient support assembly 104 includes communication modules supporting communication with various devices, such as patient-worn sensors, patient support assembly 104 mounted sensors, external sensors, internet of medical things (IoMT) physiological monitors, activity monitors, clinician devices (e.g., smart phones, computers), and/or infusion pumps. For instance, communication module 134 facilitates communicating with sensor 102 over low-energy communication channels. Example communication channels include Bluetooth, Bluetooth Smart, ZigBee, ANT, 802.15.4, Wi-Fi, Wi-Fi Direct, USB, and Controller Area Network (CAN) Bus. Patient support assembly 104 also includes communication modules 136 capable of communicating with gateway 106 via network 110.

Gateway 106 can be cloud-based. Various components instantiated as part of gateway 106 can reside in other computing platforms. Gateway 106 can be distributed across multiple computing platforms. Patient support assembly 104 includes some or all components of example computing device 801, shown and described in more detail below with reference to FIG. 7.

In some instances, one or more aspects of patient support assembly 104 may be viewed or controlled by a caregiver remotely, such as via an app on a smart phone or tablet. Some embodiments of patient support assembly 104 include a wireless display including a touchscreen for interacting with patient physiological data, as well as other communication components such as gesture recognition and/or voice recognition.

Patient support assembly 104 can include one or more connection interfaces for various types of sensors 103, enabling a "plug and play" configuration for sensors 103. Electromechanical connection interfaces can be hot-swapped as patient support assembly 104 is moved between locations, such as between two wards in a hospital. In some instances, electromechanical connection interfaces include a cover, which can be configured such that when a sensor 103 module is removed, the electromechanical interface is covered. Electrical interfaces are isolated on the patient support assembly 104-side so that the modules, e.g. sensor 103, do not need to support the size/cost of isolation. Isolation can be achieved by providing wireless power and radio frequency communications such as NFC, USB, UWB, Bluetooth, Bluetooth Low Energy, ANT, ZigBee, Wi-Fi, cellular, Wi-Fi Direct, or other communication solutions.

Power isolation can also be achieved using isolation transformers. Digital communication isolation can be achieved via isolation channels (ICs), such as the ADuM2201 (Analog Devices, Norwood, Mass.) that supports 5 kV digital isolation using magnetic coupling. Digital isolation can also be achieved using optical communication such as fiber optics or optocouplers. Further, short range communication protocols (e.g., Bluetooth Low Energy, Bluetooth Smart, Bluetooth Classic, ANT, and ZigBee) can be used to provide isolation for digital data without cost and size of an isolation interface and isolation barrier.

Depending on the use context (in-patient, out-patient, etc.), patient support assembly 104 is capable of being adjusted between various configurations of flat to upright. In some instances, patient support assembly 104 includes electro-mechanical assemblies to adjust between the various configurations. Examples of patient support assembly 104 include: beds, chairs, lifts, stretchers, surgical tables, and the like.

In some instances, mattress 132 includes an adjustable support surface 140. Generally, adjustable support surface 140 can adjust a patient's position and patient support assembly 104 can monitor how the patient reacts to those position changes. Adjustable support surface 140 can be modified with or without patient input. Typical adjustable support surfaces include one or more adjustable pressure bladders. As an example, patient support assembly 104 includes an adjustable pressure bladder near the head area 141, a second, separate adjustable pressure bladder near the torso area 142, and a third, separate adjustable pressure bladder near the feet area 144. Adjustable support surface 140 can reposition patients at risk of bed sores. Adjustable support surface 140 can also monitor where a patient's weight is, or how the patient's weight is distributed, and use feedback from sensor 102 and/or sensor 103 to inform additional actions.

In some instances, the patient support assembly 104 includes a microclimate management system 148 associated with the patient support assembly 104. Example microclimate management systems are disclosed in U.S. patent application Ser. No. 12/937,306, "Microclimate management system" and U.S. Pat. No. 9,233,038, "Patient Support with a microclimate system and a graphical user interface," the entirety of each disclosures are hereby incorporated by reference. The microclimate management system is configured to monitor and modify the environment surrounding the patient P. For example, the microclimate management system can be configured to modify the temperature and/or relative humidity surrounding the patient to achieve desired clinical benefits.

To accomplish this functionality, the microclimate management system controls an airflow system 150 associated with the patient support assembly 104. In this example, the microclimate management system can modify an amount of air flowing through the airflow system and/or a temperature and humidity of the air flowing therethrough. This, in turn, can modify a temperature of the patient that is supported by the patient support assembly 104.

Patient support assembly 104 can also include one or more patient movement/location sensors 152. As an example, patient support assembly 104 includes a plurality of load cells that provide data used to determine if the patient is moving and the patient's relative location on the bed, including if the patient P is on the edge of the bed, and/or if the patient P has exited the bed. Other movement sensors, such as radar, lidar, pressure transducers, and the like, can be used.

When a patient is assigned to a room, a caregiver can associate patient support assembly 104 with the patient or a patient identifier, such as a number assigned to the patient. This is particularly important when sensor 102 is not associated with the patient and, consequently, data that patient support assembly 104 receives from sensor 102 is not associated with any particular patient. Upon receiving data from sensor 102, patient support assembly 104 can tag or associate the received data with the patient before transmitting the data to gateway 106. Alternatively, or in addition, patient support assembly 104 communicates the patient name or identifier to gateway 106 and data are associated with the patient in that manner.

In some implementations, patient support assembly 104 includes RADAR, LIDAR, optical, or other electromagnetic sensing systems for detection of patient movement, heart rate, and respiration rate.

Gateway 106 receives and analyzes patient-specific data from patient support assembly 104 and EMR 108. Patient specific data includes physiological data as well as movement/location data. Based on the analysis, gateway 106 determines a patient status, which can be generally grouped into three categories: (1) patient location/orientation, (2) patient vitals, and (3) patient care. At a given time, more than one patient status can apply for a given category. Additionally, patient status can include one or more status from each of one or more of the categories.

Patient location/orientation/motion describes where the patient is in the room/floor and/or the patient's orientation and/or the patient's motion. Motion can range, for example, from ambulation to micromotions in the patient support apparatus that are important to avoid onset of decubitus ulcers (also known as pressure ulcers or bedsores). Both sensor 102 and patient support assembly 104 can provide data used to determine patient location and/or orientation and/or motion. Example patient location/orientation status include sleeping, deep sleeping, resting in bed, sitting up, sitting on edge of bed, walking, patient not found, etc. If the patient is sleeping, the status can be more specific to the duration of sleep and whether the patient should be left alone to continue sleeping. If the patient is not sleeping and has not slept adequately, the status can indicate that the patient should go to sleep.

Patient vitals status describes the vitals of the patient. Vital signs include clinical measurements that indicate the state of a patient's essential body functions. Thus, location, motion and orientation can be considered as a subset of vital signs. As an example, patients who have no micro motion are likely to develop pressure ulcers. As mentioned above, gateway 106 can acquire vitals data from patient support assembly 104 and/or EMR 108. Example patient vitals status include temperature, dangerous heart beat (low or high; arrhythmias), blood pressure, oxygen saturation, respiration rate, end-tidal $CO_2$, tidal volumes, etc.

Patient care status describes activities relating to care of the patient. These activities can relate to policies specific to the medical facility and/or section of the medical facility, general best practices in patient care, and/or data from the patient's EMR. Example patient care status include medication needed, routine vitals, patient should be turned, patient check-in needed, etc.

Based on the one or more patient statuses, gateway 106 determines patient-related action. For example, if the patient is sleeping, gateway 106 can determine that any pressure-reducing systems in patient support assembly 104 should be suspended so as to not wake the patient. In the same example, if the lights are on in the patient's room, gateway 106 can determine that the lighting should be dimmed. As another example, if a check-in is due for the patient, but the patient is sleeping and vitals are normal, gateway 106 can send a message to the caregiver stating as much. Another example is when the patient's temperature is above normal, gateway 106 can communicate to patient support assembly 104 to adjust the microclimate accordingly.

The system can determine that patient sleep cycles are improved with a specific head-of-bed angle and cause the angle to be adjusted (either automatically or by alerting a care-giver). The system can determine that sleep quality is disrupted by apnea events and adjust the patient support apparatus to cause breathing to restart.

Example adjustments include: changing bladder inflation, including inflation changes that roll the patient from side-to-side, activating actuators that adjust the bed, for example, the head-of-bed angle, and/or other electromechanical/audio stimulation that causes breathing to restart. Additional systems, methods, and arrangements of patient adjusting systems are provided in "Sleep disorder treatment devices, systems, and methods," U.S. application Ser. No. 15/431,985 filed Aug. 31, 2017; "Systems, methods, and devices for the treatment of sleep disorders," U.S. application Ser. No. 14/454,961 filed Aug. 8, 2014; "Dynamic apnea therapy surface," U.S. application Ser. No. 14/848,513 filed Sep. 9, 2015; and "Modular Turn Assist Apparatus and Method Therefor," U.S. application Ser. No. 62/576,275 filed Oct. 24, 2017, the entireties of which are hereby incorporated by reference.

Gateway 106 also determines an updated patient status by comparing live data received from patient support assembly 104 and EMR 108 to historical data for that patient. Broadly, updated patient status looks for changes in the patient's health, such as deterioration, which could indicate a future incident is possible. An example algorithm to determine an updated patient status between a $time_1$ and a $time_2$ is:

Updated Patient Status={Location/orientation status change between $time_1$ and $time_1$},{Patient vitals status change between $time_1$ and $time_2$},{Patient care status change between $time_1$ and $time_2$}

As an example, if patient's temperature and respiration rate have increased between measurements, additional patient-related action can include notifying the patient's caregiver about the change. In some instances, physiological data may be entered into the patient's EMR by a caregiver, such as a blood pressure measurement. Determining the updated patient status can include determining whether any new data are in the patient's EMR and, based on the new data, whether any additional patient-related action is necessary.

Gateway 106 can also improve the suggested patient-related action over time. That is, gateway 106 can analyze data to determine whether some suggested actions had a more positive influence on patient outcomes than others.

Gateway 106 includes one or more computing devices 801, shown and described below with reference to FIG. 7. In some instances, gateway 106 is in communication with displays viewable by one or more caregivers, such as a nursing station on a hospital floor. Also, gateway 106 can be in communication with caregiver-specific devices, such as hospital-issued two-way devices, pagers, mobile phones, tablet computers, etc., to deliver or communicate messages to the caregiver.

The network 110 can include any type of wired or wireless connections, wired or wireless networks, or any communication network known in the art. For example, wireless connections can include cellular network connections and connections made using protocols such as 802.11a, b, g, n and/or ac. In other examples, a wireless connection can be accomplished directly between gateway 106 and patient support assembly 104 using one or more wired or wireless protocols, such as Bluetooth, Wi-Fi Direct, radio-frequency identification (RFID), or Zigbee. Other configurations are possible.

Server 112 manages processing and communication for patient support assembly 104. Server 112 includes most or all components of example computing device 801 shown and described in greater detail with reference to FIG. 7, below. Example components and functionalities of server 112 are shown and described below with reference to FIG. 5. In some instances, gateway 106 can be instantiated as part of server 112.

Figure 4:
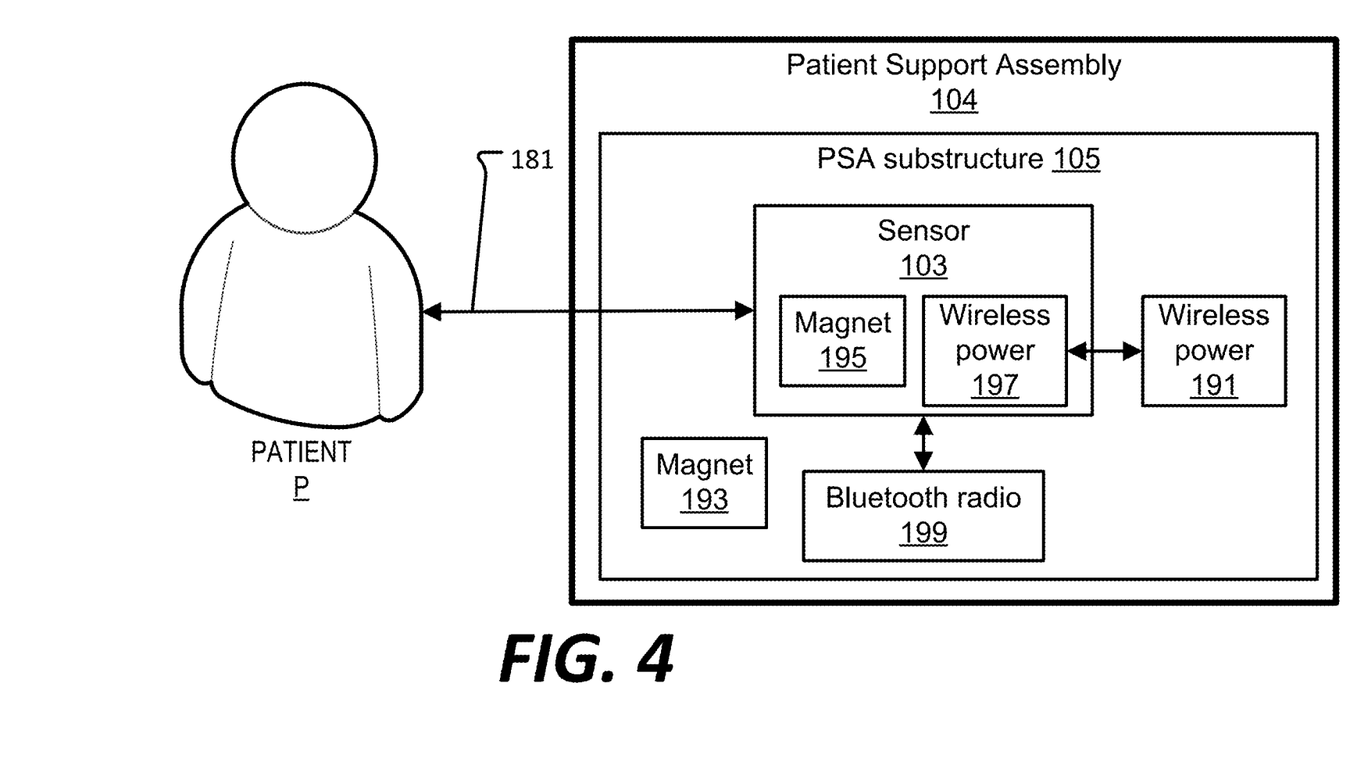
FIG. 4 is a schematic view of example components of an example patient support assembly used in the system of FIG. 1.

FIG. 4 is a schematic illustration of various components of patient support assembly 104. As shown, patient support assembly 104 includes patient support assembly (PSA) substructure 105 including sensor 103, wireless power module 191, magnet 193 and Bluetooth radio 199. Also shown is patient P. Sensor 103 obtains one or more vital signs measurements of patient P via connection 181, where connection 181 can be wired or wireless.

PSA substructure 105 includes components to receive and/or support physiological sensor modules. Receive, as used in this context, means provision for at least one of: mechanical connection, data connection, and power connection. Generally, PSA substructure 105 is a portion or part of patient support assembly 104, such as a bedrail or the back of the bed. Recesses defined by PSA substructure 105 include aspects that attach to, power, and/or communicate with sensors, such as sensor 103. Wireless power module 191 provides wireless power to sensor 103. Typically, wireless power module 191 uses a standards-based charging protocol, such as Qi and A4WP, as well as physical components, such as charging coils, configured for wireless charging. Power can be supplied by wired interfaces.

Recesses defined by PSA substructure 105 can additionally include components to retain sensor 103. For example, PSA substructure 105 can include one or more magnets 193. Sensor 103 can include one or more complementary magnets 195. PSA substructure 105 can include additional or different components to releasably hold sensor 103. Mechanical components that releasably hold the sensor can provide detection of a sensor being in place. For example, magnets may trigger a reed switch. Mechanical latches may activate a microswitch. Proximity sensors can be implemented using various sensors, such as optical, ultrasound, and infrared sensors.

PSA substructure 105 can include various components to communicate with sensor 103. Data communication between PSA substructure 105 and sensor 103 can include authentication, patient correlation, physiological data transfer, patient identification, and the like. Components to communicate with sensor 103 can be wired or wireless. FIG. 4 shows an example wireless data communication module, Bluetooth radio 199, as a component to communicate with sensor 103.

In some instances, PSA substructure 105 is an adjustable assembly such that PSA substructure 105 can be positioned proximal to patient P's body. Adjustment of PSA substructure 105 occurs independent of patient support assembly 104. Thereby, sensors (such as sensor 103) supported by PSA substructure 105 are positioned proximal to patient P and that position can be maintained for an extended period of time.

Figure 5:
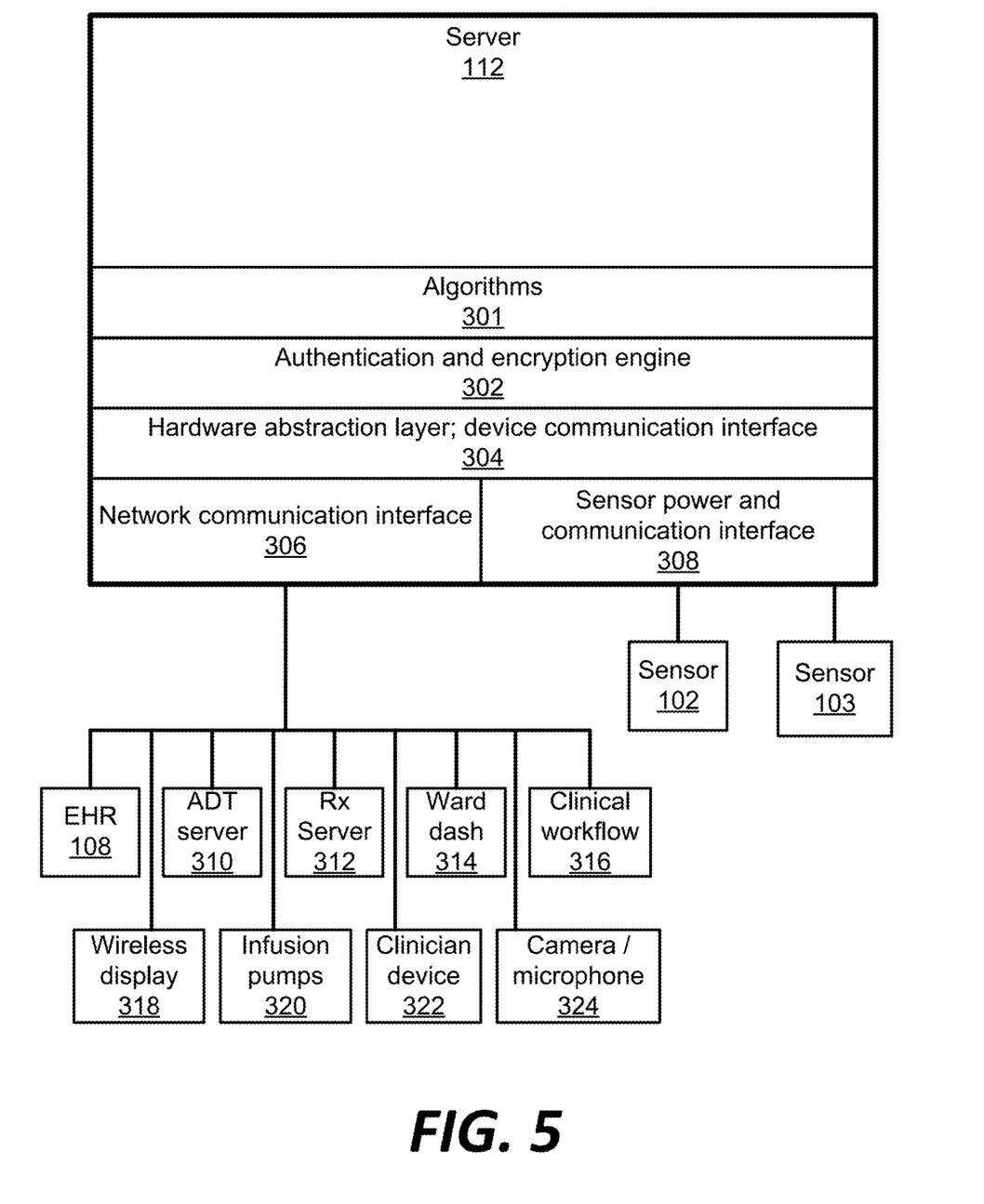
FIG. 5 is a schematic view of an example server used in the system of FIG. 1.

FIG. 5 is a schematic illustration of server 112 as well as various external components of an example patient care environment. Typically, server 112 is positioned on patient support assembly 104. Server 112 includes one or more components of example computing device 801. As shown schematically in FIG. 5, server 112 includes algorithms 301, authentication and encryption engine 302, hardware abstraction layer/device communication interface 304, network communication module 306, and sensor power/communication interface 308. Various components instantiated as part of server 112 can reside in other computing platforms. Server 112 can be distributed across multiple computing platforms. Software functions described herein may be accomplished in various locations. For example, some server 112 functions can be run on gateway 106 and vice-versa.

Generally, server 112 supports control of, and manages communications with, various components in the example patient care environment and patient support assembly 104. For instance, components include admissions, discharges, transfers (ADT) and EHR servers and sensors such as sensor 102 and/or sensor 103. Server 112 can also adjust components of patient support assembly 104, such as lie angle and inflatable compartments.

Algorithms 301 receive and process parameters relating to patient P and patient support assembly 104. As an example, algorithms 301 can determine actions, such as patient support assembly 104 adjustments, based on one or more of: vital signs, patient age, diagnosis, patient movement, and physician orders. For example, a patient at risk for aspiration, algorithms 301 cause patient support assembly 104 to set, or prompt the clinician to set, a head of bed angle to a minimum angle, such as 30 degrees.

Algorithms 301 can adjust or suggest adjustments to one or more alarm limits, and/or prioritize alarms, as a function of medication prescribed to patient P, patient diagnosis, and/or angle of patient support assembly 104. Algorithms 301 can hold or mute alarms based on patient movement and/or clinician entry. Algorithms 301 can also suspend, disable, or decrease the volume of other systems, such as patient monitoring devices and infusion pumps.

As an example, if a patient is brushing teeth (where muscle artifacts can appear as ventricular tachycardia), alarms for ventricular tachycardia are suspended. As another example, if a patient is moving, respiration rate alarms are suspended. As another example, if a patient is eating, ECG signal alarms are suspended because noise is typically expected. Such multi-alarm processing helps avoid false alarms. As another example, alarms are muted when the patient is asleep and the alarms are not critical.

Algorithms 301 perform other actions related to patient P and the patient care environment. For instance, algorithms 301 can search and display prior patient information from other health care facilities and/or electronic health records. By connecting to a patient's EHR, algorithms 301 determine pharmacological data, such as prescribed and/or administered medications, and can modify alarm limits if the medication is known to increase or decrease particular vital signs, such as heart rate and respiration rate. Algorithms 301 can use vital signs data and EHR data to determine if patient P suffers from side-affects associated with overmedication. For instance, if the patient's premature ventricular contractions (PVC) rate increases after Levothyroxine is administered (where hyperthyroidism has a high incidence of premature ventricular contractions).

Additionally, algorithms 301 can use data from the patients ADT/EHR for the current admission to determine recent information such as diagnosis, treatment, and prescriptions, as well as prior vital sign measurements such as ECG strips, blood pressure, weight, respiration rate, and heart rate. Algorithms 301 can search for this information in the background when a patient is admitted so the information is available to the doctor on demand.

Algorithms 301 can also initiate an alert to a clinician if an expected event does not occur. For example, if a hypertensive patient is given a vasodilator (typically in a hypertensive crisis), algorithms 301 initiate a request to take blood pressure measurements at an increased frequency. Then, algorithms 301 can initiate a clinician alert if a change in blood pressure does not occur. As another example, if patient P is given norepinephrine, which increases blood pressure, then algorithms 301 can raise blood pressure alarm levels for a period of time.

Algorithms 301 can also continuously monitor when alarms occur, and for what duration, and determine if the alarms are clinically actionable. For example, if the patient frequently has an SPO2 saturation reading that dips below a threshold of 90 for 3-5 seconds, and then returns to non-alarm levels, the SPO2 alarm hold-off is adjusted to 5 seconds. As another example, if a patient's SPO2 level is continuous at 88, but other vital signs do not indicate a negative trend, then SPO2 alarm limits may be adjusted from 88 to 90. Algorithms 301 can search the patient's EHR to determine a patient diagnosis, such as chronic obstructive pulmonary disease (COPD), age, and prior SPO2 levels to determine whether an SPO2 alarm of 88 is a safe and effective alarm limit to reduce non-actionable alarms.

Algorithms 301 can manage multiple alarms from multiple sources. Depending upon the implementation, patient support assembly 104 can receive alarm data from devices in the patient care environment, such as PSS, infusion pump, and vital signs sensors. Algorithms 301 can advise clinicians which patients need attention. Algorithms 301 can also prioritize the various alarms for clinician notification.

Algorithms 301 can monitor heart-beat variability, gathering data from available sources such as ECG, SPO2, RADAR, accelerometers, etc. Algorithms 301 can analyze heart-beat data using various methods, such as spectrum of intervals (SOI), resampled interval series (RIS), tachometer spectrum, spectrum of counts (SOC), Lomb spectrum, deceleration capacity (DC), acceleration capacity (AC), standard deviation to next normal beat (SDNN), SDNN Index (mean of 5-minute standard deviations of NN), SDANN index (standard deviation of all the 5-minute NN interval means), Lagrange, r-MSSD (root-mean-square successive difference), and PNN50 (the percentage of differences between successive NN intervals over 24 hours that are greater than 50 ms).

Algorithms 301 can use heart rate variability and/or other vital signs to determine a risk score for the patient. Patient support assembly 104 or another device in the patient care environment can display that risk score. As an example, algorithms 301 can determine that the patient is 3 times more likely to develop sepsis than the standard population. Heart-beat variability data can also be used to monitor sleep quality, patient decline, and patient readiness for transfer or discharge. Sleep quality is a metric that can be used as part of determining patient decline (including mental state and suicidality) or readiness for transfer or discharge.

Algorithms 301 can analyze data to identify groupings of changes that may indicate medical emergency if not immediately attended to. Example groupings include Cushing's Triad, Beck's Triad, and CO2 narcosis. Cushing's Triad is an increase in systolic pressure, bradycardia, and irregular respiration and is applicable to patients diagnosed with intracranial pressure (ICP). Beck's Triad is low arterial blood pressure, increased venous pressure (e.g., distended neck veins), and muffled heart sounds. CO2 narcosis applies to obese or extremely obese patients and includes high $E_TCO_2$, low respirations, and shallow respirations.

Algorithms 301 can receive and process other types of data with a focus on ease of use and/or patient comfort. Example processes include voice and gesture recognition, noise cancellation, logging, and software updates for patient support assembly 104 and/or sensor 102, 103. Voice and/or gesture recognition can be used to provide hands-free control of patient support assembly 104 by patient P. For instance, rather than reaching for a bed control, patient P can speak instructions to patient support assembly 104 to raise the feet portion of the bed. Alarm noise cancellation is a system that learns the alarm sounds in the room, predicts the next alarm, and creates the opposite pressure (sound) wave in the area of the patient's ears. Algorithms can also track sleep quality and vital signs and adjust patient support assembly 104 to optimize sleep quality and vital signs.

Algorithms 301 can enable server 112 to support Simple Network Management Protocol (SNMP) services. While SNMP is typically used for providing information and control of network devices, SNMP can be used to provide status of the patient as well as the monitoring device. Managed devices are accessed via a management information base (MIB), and MIB objects are generally accessed through SNMP. SNMP allows monitoring of a multitude of devices by a management host with a small impact on the managed devices.

Example server 112 also includes hardware abstraction layer 304. Hardware abstraction layer 304 includes communication interfaces and drivers providing a uniform view and interface to the various hardware devices to upper-layer software. Hardware abstraction layer 304 enables "plug and play" support, which allows supported devices (e.g., sensor 103) to register with the patient support assembly 104 and begin communication without user intervention.

Example server 112 also includes authentication and encryption engine 302. Validation can be used to ensure that a product, consumables it uses, firmware it runs, accessories that support it, and the network nodes it connects to are not cloned, counterfeited, or tampered with. Authentication and encryption engine 302 ensure that only validated and/or authenticated devices connect to patient support assembly 104. Authentication and encryption engine 302 also ensures that data transmitted to or from those devices are encrypted. Additionally, authentication and encryption engine 302 can validate patient support assembly 104 to the network.

As an example, authentication and encryption engine 302 might support 802.1x to provide certificate-based authentication of the device, pre-shared key, LDAP, or other authentication solutions. Authentication and encryption engine 302 may provide an encryption engine that includes the Advanced Encryption Standard (AES), Data Encryption Standard (DES), 3DES, Secure Hash Algorithms (SHA), Elliptic-Curve Cryptography (ECC), or any other encryption solution. Authentication and encryption engine 302 may cause data to be encrypted while at rest and during transport. Further, it may provide end-to-end encryption, including application-level encryption. Authentication and encryption engine 302 may also use crypto-authentication chips, such as the Atmel ATAES132A. These devices, with hardware-based key storage, ensure that a product, consumables it uses, firmware it runs, accessories that support it, and the network nodes it connects to are not cloned, counterfeited, or tampered with. Keys can be based on SHA, AES, ECC or other cryptographic solutions.

In some implementations, patient support assembly 104 includes RADAR for detection of patient movement, heart rate, and respiration rate. In certain examples, a radar module uses radio waves to determine various characteristics of objects. In this example, the radar module is configured to detect various aspects of the patient P, as described herein. One example of the radar module 120 is IR1642, available from Texas Instruments Inc., Dallas, Tex.

In typical operation, a radar signal is transmitted toward the patient and is used to detect a patient status, such as a patient position, a patient incontinence condition, a patient ambulation, and/or a physiological condition of the subject. One example of the radar signal includes a millimeter wave, such as a signal having a band of spectrum between abound 30 GHz and about 300 GHz. Other examples of the radar signal include microwaves and ultrawideband (UWB).

Algorithms 301 process data from radar to obtain images of the patient from multiple angles. Algorithms 301 can use the processed data to track patient movement, heart rate, and respiration rate. In certain examples, the system can detect one or more body portions of the patient by analyzing the radar signal and predicting an upcoming position of the patient based on the analysis Server 112 also includes network communication interface 306. Generally, network communication interface 306 facilitates communication between patient support assembly 104 and various devices in example patient care system 100, including networked devices such as EHR 108 and clinician interfaces such as personal computers, laptops, carts-on-wheels, and the like. FIG. 5 shows example devices that communicate with server 112 via network communication interface 306. These devices include EHR database 108, ADT server 310, prescription server 312, ward dash 314, clinical workflow 316, wireless display 318, infusion pumps 320, clinician device 322, and camera/microphone 324.

Server 112 also includes sensor power and communication interface 308. Sensor power and communication interface 308 facilitates sending and receiving data from wired and wireless sensors (e.g., sensor 102, sensor 103) in example patient care system 100. Data can be communicated over a power interface, including over a wireless power interface.

Figure 6:
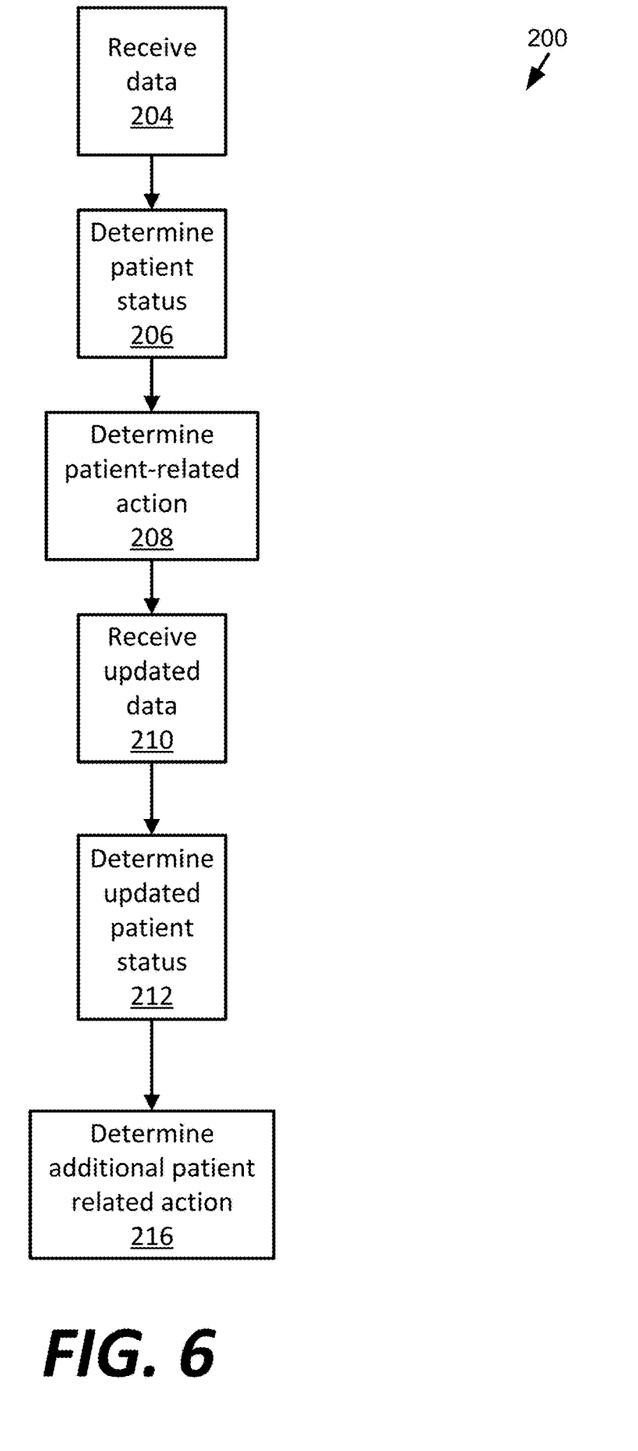
FIG. 6 illustrates an example method for patient monitoring.

Referring now to FIG. 6, an example process 200 illustrating operation within patient care system 100 is shown. Other processes can include more or fewer operations.

The example process 200 begins by receiving data (operation 204). Typically, data include demographics, physiological data, location data and/or orientation data. Additionally, data include historical data and other data, such as diagnosis, treatment, and medications, entered into a patient's EMR.

Upon receiving one or more patient-related data, patient status is determined (operation 206). Patient status describes one or more aspects of the patient. Determining patient status can include analyzing raw data, such as physiological data, received from a patient support assembly or EMR, as well as comparing raw data to normal values.

Based on the patient status, patient-related action is determined (operation 208). Determining patient-related action can include comparing one or more aspects of the patient status to a table or list suggesting action given a particular status. In some instances, more than one action is determined, such as transmitting a communication and altering an environmental condition in the patient's room. In some instances, a gateway device carries out the patient-related action determined in operation 208.

After a given period of time, updated data are received (operation 210). The period of time can be fractions of a second, seconds, minutes, or hours. In some instances, the gateway device referenced above transmits a request for updated patient-related data to the patient support assembly and/or electronic medical records database. Alternatively, updated patient-related data are pushed to the gateway.

Updated patient status is then determined using the updated data (operation 212). Similar to the patient status, updated patient status can include more than one descriptor of the patient's status. The updated patient status can be based solely on the updated data. Alternatively, or in addition, the updated patient status can be based on a comparison of data received in operation 204. In this way, patient health trends can be identified.

Using the updated patient status, additional patient-related action is determined (operation 216). Similar to determining patient-related action (operation 208), determining additional patient-related action can include comparing one or more aspects of the updated patient status to a table or list suggesting actions corresponding to given patient status. Again, more than one action can be determined. In some instances, the gateway device executes the additional patent related action.

Figure 7:
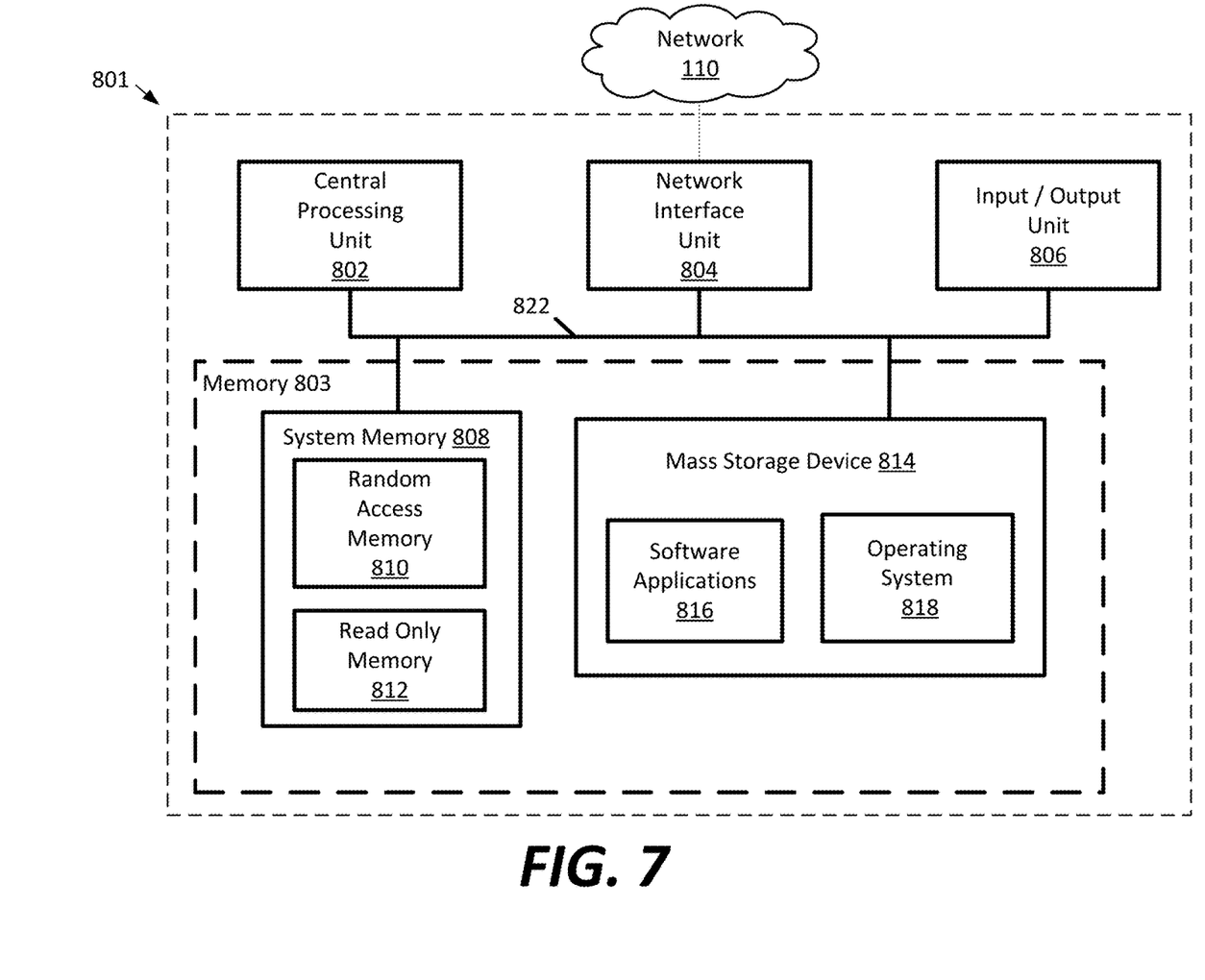
FIG. 7 shows example physical components of a computing device hosting the client system manager module of the display shown in FIG. 1.

FIG. 7 shows one example of the computing device 801 of the gateway 106. As shown, example computing device 801 hosts system manager 300 that is capable of executing the operations of example process 200. The patient support assembly 104 can include a different software application configured to manage communication with sensor 102 and gateway 106 and capable of performing the operations of patient support assembly 104 described above.

As illustrated, the example computing device 801 includes at least one central processing unit ("CPU") 802, memory 803, and a system bus 822 that couples memory 803 to the CPU 802. Memory 803 includes system memory 808 and mass storage device 814. System memory 808 includes a random access memory ("RAM") 810 and a read-only memory ("ROM") 812. A basic input/output system that contains the basic routines that help to transfer information between elements within the example computing device 801, such as during startup, is stored in the ROM 812. Memory 803 further includes mass storage device 814. Mass storage device 814 is able to store software applications 816 and data.

Mass storage device 814 is connected to CPU 802 through a mass storage controller (not shown) connected to the system bus 822. Mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. The network 110 may be a protected network, as discussed above. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software applications 816, that when executed by the CPU 802, cause the example computing device 801 to provide the functionality of the example computing device 801 discussed in this document. For example, the mass storage device 814 and/or the RAM 810 can store software instructions that, when executed by the CPU 802, cause the example computing device 801 to display received data on the display screen of the example computing device 801.

Although various embodiments are described herein, those of ordinary skill in the art will understand that many modifications may be made thereto within the scope of the present disclosure. Accordingly, it is not intended that the scope of the disclosure in any way be limited by the examples provided.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A patient monitoring and support system, comprising:
a patient support assembly configured to support a patient;
a patient status device configured to obtain patient status data; and
a control module including:
a processing unit; and
memory having stored thereon instructions that, when executed by the processing unit, cause the control module to:
receive the patient status data from the patient status device;
analyze the patient status data to determine a condition of the patient;
based on the condition of the patient, adjust an alarm setting, including to prioritize alarms when the patient status data indicates a change in the condition of the patient;
based on the change in the condition of the patient, adjust a position of the patient support assembly, the position of the patient support assembly being a head-of-bed angle; and
further adjust the alarm setting, including to adjust one or more alarm limits as a function of the head-of-bed angle.

2. The patient monitoring and support system according to claim 1, wherein the patient status data is selected from the group consisting of: vital sign data, patient diagnosis data, patient treatment data, patient position data, patient movement data, patient history data, patient demographic data, patient alarm data, and pharmacological data, and
wherein the control module is configured to adjust the alarm setting based on the pharmacological data.

3. The patient monitoring and support system according to claim 2, the memory further storing instructions that, when executed by the processing unit, cause the control module to determine based on the vital sign data, whether the patient is experiencing a side effect associated with overmedication.

4. The patient monitoring and support system according to claim 1, wherein the patient status data includes patient movement data;
wherein the control module is configured to adjust the alarm setting by holding an alarm for a period of time determined by the patient movement data; and
wherein the alarm is a respiration rate alarm.

5. The patient monitoring and support system according to claim 1, the memory further storing instructions that, when executed by the processing unit, cause the control module to, upon determining that the patient is at risk for aspiration, automatically adjusting a head of bed angle to at least 25 degrees.

6. The patient monitoring and support system according to claim 1, the memory further storing instructions that, when executed by the processing unit, cause the control module to, upon determining that the patient is at risk for aspiration, transmit a clinician notification, the clinician notification including a recommendation for adjusting a head of bed angle to at least 25 degrees.

7. The patient monitoring and support system according to claim 1, the memory further storing instructions that, when executed by the processing unit, cause the control module to authenticate a physiological sensor device.

8. The patient monitoring and support system according to claim 7, the patient monitoring and support system defining a sensor receiving cavity sized to receive the physiological sensor device, the sensor receiving cavity including a magnet.

9. The patient monitoring and support system according to claim 8, the sensor receiving cavity including a wireless charging module configured to provide power to the physiological sensor device.

10. The patient monitoring and support system according to claim 9, the sensor receiving cavity including a data communication module configured to enable data transmission between the physiological sensor device and the patient monitoring and support system.

11. The patient monitoring and support system according to claim 1, wherein the patient status data includes pharmacological data, and wherein the control module is configured to further adjust the alarm limits when the pharmacological data predicts a change in the patient status data.

* * * * *